| United States Patent [19] | [11] | 4,145,549 |
|---|---|---|
| Stadler | [45] | Mar. 20, 1979 |

[54] PROCESS FOR PREPARING OXAZOLO[3,2-a]PYRROLO[2,1-c]PYRAZINE DERIVATIVES

[75] Inventor: Paul Stadler, Biel-Benken, Switzerland

[73] Assignee: Sandoz Ltd., Basel, Switzerland

[21] Appl. No.: 757,616

[22] Filed: Jan. 7, 1977

[30] Foreign Application Priority Data

Jan. 12, 1976 [CH] Switzerland .................... 269/76

[51] Int. Cl.$^2$ .................. C07D 519/02; C07D 457/12; C07D 207/08; C07D 401/12
[52] U.S. Cl. ....................... 544/346; 546/69; 546/68; 260/326.43; 260/326.46; 260/326.25
[58] Field of Search ......... 260/268 PE, 285.5, 326.43, 260/326.46, 265 R, 326.25; 544/346

[56] References Cited

U.S. PATENT DOCUMENTS

| 2,533,698 | 12/1950 | Stoll et al. | 260/285.5 |
|---|---|---|---|
| 3,752,814 | 8/1973 | Fluckiger et al. | 260/285.5 |
| 3,755,328 | 8/1973 | Stadler et al. | 260/285.5 |
| 4,000,139 | 12/1976 | Stutz et al. | 260/285.5 |
| 4,091,099 | 5/1978 | Lehr et al. | 544/346 |

FOREIGN PATENT DOCUMENTS

| 805237 | 3/1974 | Belgium | 260/285.5 |
|---|---|---|---|
| 822729 | 5/1975 | Belgium | 544/346 |
| 830441 | 12/1975 | Belgium | 544/346 |
| 837312 | 7/1976 | Belgium | 544/346 |

OTHER PUBLICATIONS

Stuetz et al., Chem. Abs. vol. 85: 160399v (1976).
Morrison et al., Organic Chemistry 2nd Edit. (1969).
Theitheimer; Synthetic Methods of Org. Chem. vol. 14:446, vol. 15: 358, vol. 14: 613.
Floss et al., Experientia, vol. 30, pp. 1369-1370.
Chemiakine et al.; Bull. Soc. Chim. France pp. 530-536 (1959).
Chemie der Mutterkornallieloide, pp. 152-170.

*Primary Examiner*—Alton D. Rollins
*Assistant Examiner*—Mary Lee
*Attorney, Agent, or Firm*—Gerald D. Sharkin; Robert S. Honor; Thomas O. McGovern

[57] ABSTRACT

The present invention provides a novel cyclization process useful for the production of the peptide moiety of an ergotalkaloid.

22 Claims, No Drawings

PROCESS FOR PREPARING OXAZOLO[3,2-a]PYRROLO[2,1-c]PYRAZINE DERIVATIVES

The present invention relates to peptides, especially aminocyclols of formula I,

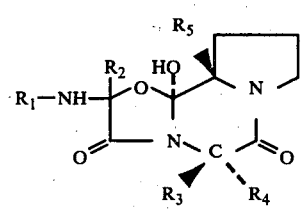

wherein $R_1$ to $R_5$ are inert radicals.

In particular the invention provides a novel process for the production of a compound of formula I which comprises intramolecularly cyclizing a compound of formula II,

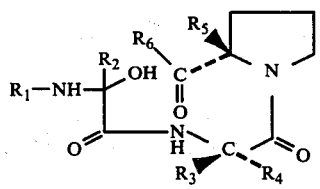

wherein
$R_1$ to $R_5$ are as defined above, and
$R_6$ is a leaving group.

The intramolecular cyclization may be effected under solvolytic conditions for cyclization with the splitting off $R_6H$. The conditions should be mild because of the sensitive nature of the system.

A non-aqueous medium may be used. However, preferably the reaction is effected in an aqueous medium, preferably at a pH of from 7.3 to 10, especially from 7.3 to 8, in the presence of e.g. an alkali metal salt of a carboxylic acid, e.g. potassium or sodium acetate, citrate or tartrate. An inert water-miscible solvent may be present such as acetone, dimethylsulphoxide, dimethoxyethane, dioxane, tetrahydrofuran, dimethylformamide or dimethylacetamide.

The reaction temperature may be conveniently from 0° to 30°, e.g. room temperature.

$R_6$ is preferably N-succinimidoxy, phenoxy or phenylthio. It is to be appreciated that the phenoxy or phenylthio group may be substituted by at least one lower alkyl, e.g. methyl, halogen, e.g. bromine, chloride or fluorine, and/or nitro group.

Preferably the groups are in the ortho and/or para positions when there are 1 to 3 substituents. In the case of fluorine and chlorine there may be up to 5 substituents.

Examples of suitable groups are N-succinimidoxy, pentafluorophenoxy, pentachlorophenoxy, a radical A,

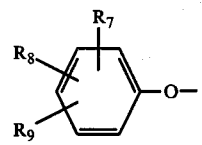

wherein
$R_7$ is nitro,
$R_8$ is hydrogen, chlorine or methyl, and
$R_9$ is hydrogen or nitro,
or p-chlorophenylthio. Preferred groups are o,p-dinitrophenoxy, o-methyl-o'-p'-dinitrophenoxy, pentachlorophenoxy and especially p-nitrophenoxy.

$R_1$ may be, for example, an amino-protecting group, preferably one that may be removed under — hydrogenolytic conditions, e.g. carbobenzoxy. Alternatively, $R_1$ may be a lysergic acid residue which may conveniently be in protected form. It is to be appreciated that the term "acid," as used herein, covers corresponding 9,10-dihydro derivatives, 2-halo derivatives, 13-bromo derivatives, and 6-($C_{2-6}$)-alkyl and 6-phenylalkyl ($C_{7-11}$) derivatives and 1-($C_{1-4}$)alkyl and allyl derivatives. A suitable protected derivative is the corresponding 2,3-dihydrolysergic acid derivative, which has the nitrogen atom at the one position, if not blocked otherwise, e.g. by alkyl or allyl, blocked by an acetyl group.

$R_2$ may be, for example, the lower alkyl moiety preferably containing 1 to 4 carbon atoms. Examples of suitable groups are methyl, ethyl, n-propyl and ispropyl.

$R_3$ and $R_5$ may be the same or different and may be, for example, hydrogen or lower alkyl, preferably of 1 to 5 carbon atoms, especially 1 to 4 carbon atoms, and particularly methyl.

$R_4$ may be, for example, hydrogen, lower alkyl, phenyl, benzyl or benzyl mono-substituted by lower alkoxy. Lower alkyl is preferably of 1 to 6, and especially of 1 to 4 carbon atoms. The lower alkoxy radical is preferably of 1 to 4 carbon atoms, especially methoxy and is preferably in the para-position.

It is to be appreciatd that any of the other carbon atoms in the aminocyclol of formula I may also bear inert substituents The compound of formula II may be reacted in optically pure form. Thus a compound of formula IIa,

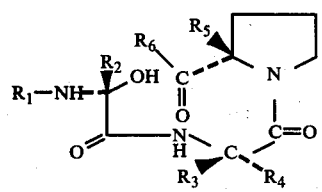

will cyclize to produce a compound of formula Ia,

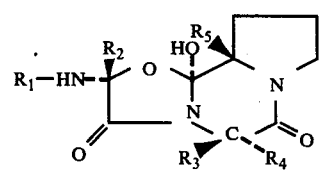

i.e. in "natural" form, i.e. the absolute configurations of the asymmetric carbon atoms are the same as those of the aminocyclol of dihydroergotamine.

A compound of formula IIb,

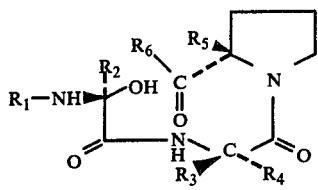

IIb will cyclize to produce to produce a compound of formula Ib,

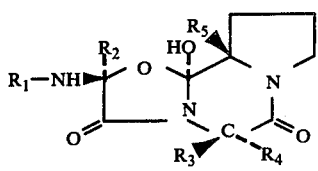

Ib i.e. in the known "aci" form.

The "aci" form and the "natural" form may be equilibrated under mild acidic conditions in known manner, as described in Example 2.

The compound of formula II is conveniently reacted as a diastereoisomeric mixture of compound of formulae IIa and IIb in which case both the "natural" and "aci" forms are produced, which can be separated in conventional manner.

The compounds of formula II are, in general, unstable, and may be reacted in crude form as the reaction product of a process comprising replacing, under oxidizing or mild hydrolytic conditions, a group $R_{10}$ by hydroxy in a compound of formula III,

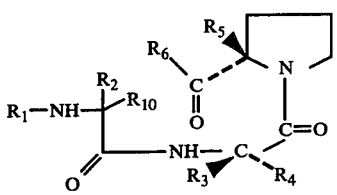

III wherein
$R_1$ to $R_6$ are as defined above, and
$R_{10}$ is a group capable of being split off under oxidative or mild hydrolytic conditions, respectively.

$R_{10}$ may be, for example, halo, e.g. chlorine, bromine or iodine, isocyanate, $CH(CH_3)$—OH or preferably $CH_2OH$. The reaction may be effected in conventional manner for such hydrolysis and oxidation reactions. It is to be appreciated that under basic hydrolytic conditions the compound of formula III may be converted directly into a compound of formula I. The reaction is preferably an oxidizing reaction. For example, lead tetraacetate may be used [see Chem. Ber. 103, 2314, (1970)]. In this instance, racemization at the carbon atom to which $R^2$ is bound occurs during the reaction. Thus when an optically pure compound of formula III is used, a diastereoisomeric mixture will result, which can be used in the preparation of "natural" and "aci" forms of compounds of formula I.

A compound of formula III may be obtained by esterifying a compound of formula IV,

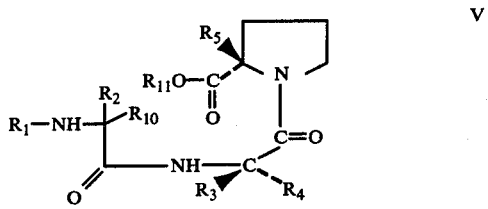

IV wherein $R_1$ to $R_5$ and $R_{10}$ are as defined above, in conventional manner, e.g. in the presence of a compound $R_6H$ and dicyclohexylcarbodiimide.

A compound of formula IV may be obtained by splitting off, under acidic conditions, a protecting group $R_{11}$ from a compound of formula V,

V wherein
$R_1$ to $R_5$ and $R_{10}$ are as defined above, and
$R_{11}$ is a group capable of being split off under acidic conditions.

The reaction may be effected in conventional manner. $R_{11}$ may be, for example, tert.-butyl.

A compound of formula V may be obtained in conventional manner by condensing a compound of formula VI,

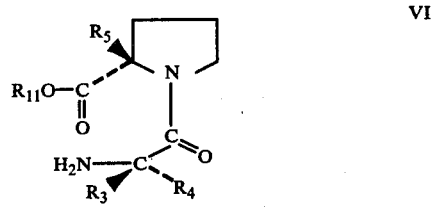

VI wherein $R_3$, $R_4$, $R_5$ and $R_{11}$ are as defined above, with a compound of formula VII,

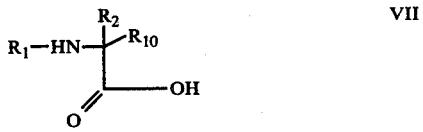

VII wherein $R_1$, $R_2$ and $R_{10}$ are as defined above.

The reaction may be effected in conventional manner for joining two amino acids, e.g. in the presence of dicyclohexylcarbodiimide. The compound of formula VII, if desired, may be in activated form, e.g. after reaction with N-hydroxy-succinimide.

If the compound of formula VII is in racemic form then the compound of formula V will be a diastereoisomeric mixture which may be separated in conventional manner. As, however, racemization may anyway occur on the production of a compound of formula II from a compound of formula III, it may be convenient not to carry out any separation at this stage.

A compound of formula VII may be produced as described in the Examples hereinafter, or in known manner.

A compound of formula VI may be produced by splitting off, under hydrogenolytic conditions, a group $R_{12}$ from a compound of formula VIII,

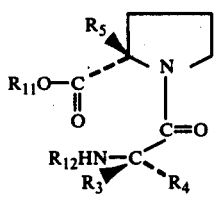

VIII wherein — $R_3$, $R_4$, $R_5$ and $R_{11}$ are as defined above, and $R_{12}$ is a group capable of being split off under hydrogenolytic conditions, e.g. carbobenzoxy.

It is to be appreciated that $R_{11}$ should conveniently be chosen so as not to be the same as $R_{12}$.

A compound of formula VIII may be produced by condensing a compound of formula IX,

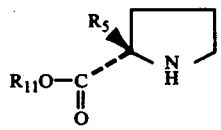

IX wherein — $R_5$ and $R_{11}$ are as defined above, with a compound of formula X,

X wherein — $R_3$, $R_4$ and $R_{12}$ are as defined above.

A compound of formula X may be a natural, optically pure, amino acid, in which case, the resulting compound of formula VIII may be optically pure.

A compound of formula IX may be produced as described in Examples 1(a) and 1(b) hereinafter.

Insofar as the preparation of any starting material is not particularly described, these may be produced and purified in known manner.

Compounds of formula I are in general known as intermediates for the production of ergot alkaloids, e.g. dihydroergotamine and dihydroergonine. Compounds of formula I, wherein $R_1$ is a protected lysergyl residue, may be converted into ergot alkaloids in manner known per se. For example, a 2,3-dihydrolysergic acid residue can be converted into a lysergyl acid residue by treatment with Raney-Nickel poisoned with sodium arsenate, or mercuric (II) acetate, if necessary removing any 1-acetyl group present by hydrolysis.

Compounds of formulae Ia or Ib, wherein $R_1$ is an amino protecting group, may be converted into the natural or "aci" forms, respectively, of compounds of formula

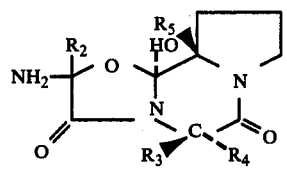

in the form of an acid addition salt, e.g. the hydrochloride, in conventional manner, e.g. by hydrogenation in a methanolic mineral acid solution with a palladium catalyst. These may be condensed with lysergic acid,9,10-dihydrolysergic acid or a reactive functional derivative thereof to afford the corresponding ergot alkaloids.

In the following Examples all temperatures are in degrees Centigrade and are uncorrected. High vacuum means 0.01 mm Hg.

The individual optical isomers of compounds of formulae III, IV and V are referred to as tripeptides, or tripeptide esters, I and II.

EXAMPLE 1

Aci(2S,5S,10aS,10bS) and natural (2R,5S,10aS,10bS) forms of 2-carbobenzoxyamino-2-methyl-5-benzyl-10b-hydroxy-3,6-dioxo-octahydro-8H-oxazolo[3,2-a]pyrrolo-[2,1-c]pyrazine

[Compounds of formula I, wherein $R_1 = C_6H_5.CH_2.O.CO$; $R_2 = CH_3$; $R_3 = H$; $R_4 = C_6H_5CH_2$; $R_5 = H$].

6.1 g of crude N-(N-carbobenzoxy-DL-α-hydroxyalanyl)-L-phenylalanyl-L-proline p-nitrophenyl ester obtained in step hi), hii) or hiii) below, in 300 ml acetone, is treated with a 10% (w/v) potassium tartrate solution (having pH = 7.9). The reaction mixture is stirred for 18 hours at room temperature, and worked up by the addition of 10% (w/v) tartaric acid solution until the reaction mixture is at a pH of 5 and extraction with methylene chloride. The product obtained on concentration is crystallized from ethyl acetate or an ethyl acetate/diisopropyl ether mixture (3:1; v/v) yielding, after drying at 90° in a high vacuum, the aci-form of the title compound (M.Pt. 206°-208°; decomposition); $[\alpha]_D^{20} = -28°$ (c = 0.5 in $CH_3OH$).

The mother liquors of the crystallizations are extracted three times with 400 ml 0.5 N sodium carbonate. The sodium carbonate extracts are extracted with methylene chloride.

The methylene chloride extracts are concentrated, dried and chromatographed on silicagel eluting, with methylene chloride containing 4–6% (v/v) acetonitrile side products, and, with methylene chloride containing 10 to 14% (v/v) acetonitrile the title compound in the natural form. The natural form is purified further by chromatography on aluminium oxide (activity II–III) using methylene chloride/acetone (1:1 v/v) as eluant. The first fractions are concentrated and crystallized using a mixture of damp ethyl acetate and a little diisopropyl ether to yield the pure title compound in natural form; M.Pt. 170°-172°$[\alpha]_D^{20}= +9.8$ (c = 1.6 in $C_2H_5OH$).

Further amounts of the aci-form of the title compound may be obtained:

(i) from the above-mentioned sodium carbonate extracts. After washing with methylene chloride, these extracts are adjusted to pH 4–5 by the addition of tartaric acid and extracted with methylene chloride. These extracts are dried, concentrated and chromatographed on silica gel. The fractions eluted with methylene chloride containing 6% acetonitrile elute paranitrophenol and are discarded. Elution with methylene chloride containing 20% (v/v) acetonitrile gives the aci-form which after concentration is crystallized from ethyl acetate; and (ii) from the above-mentioned chromatography using methylene chloride and 4–14% (v/v) acetonitrile. Further elution with methylene chloride and 14–20% (v/v) acetonitrile gives fractions which are washed with 0.5 N sodium carbonate and then, after concentration, crystallized from ethyl acetate to yield the aci-form.

The starting material may be obtained as follows:

(a) N-benzoxycarbonyl-L-proline tert.-butyl ester 126.9 (1 mol) of oxalyl chloride is added dropwise over 15 minutes to a stirred mixture of 200 ml absolute dimethylformamide and 500 ml absolute acetonitrile cooled to $-20°$. The solution is stirred for a further 15 minutes at $-20°$ and then 249 g (1 mol) N-carbobenzoxy-L-proline is added. After 15 minutes of stirring, the mixture is treated dropwise with a mixture of 250 ml of absolute tert.-butanol and 200 ml absolute pyridine at such a rate that the temperature of the mixture does not rise above $-15°$. Cooling of the mixture is then stopped, and the mixture is maintained at room temperature for 3 hours. The mixture is worked up by partitioning between 2N sodium carbonate solution and methylene chloride and obtaining the heading compound from the methylene chloride phase as an oil $n_D^{23} = 1.5015$ which slowly crystallizes out.

(b) L-proline tert.-butyl ester [compound of formula IX]

The 267 g of the crude product obtained in step a) in 1.5 l ethanol is catalytically hydrogenated in the presence of 40 g of 5% (w/w) palladium/charcoal catalyst at normal pressure and room temperature to give the heading compound as a colourless oil; B.Pt. 43°–46° (0.01 mm Hg) $n_D^{20} = 1.4435 [\alpha]_D^{20} = -41.7°$ (c = 2; $C_2H_5OH$).

(c) N-carbobenzoxy-L-phenylalanyl-L-proline tert.-butyl ester [compound of formula VIII]

157 g of N-carbobenzoxy-L-phenylalanine in 500 ml methylene chloride and 300 ml absolute diethyl ether is treated at 15°–18° C. with 85.5 g L-proline tert.-butyl ester in 100 ml diethyl ether over 5 minutes, and then with 114 g of dicyclohexylcarbodiimide in 150 ml of diethyl ether over 15 minutes, both additions being at such a rate that the reaction mixture temperature does not rise above 18° C. The resultant mixture is stirred for a further hour at room temperature, and filtered, the solid residue being washed with ether. The filtrate is washed with, in turn, 2N hydrochloric acid, water, potassium bicarbonate, and then water, each washing being extracted with diethyl ether. All the organic phases are combined, dried over sodium sulphate and concentrated to yield an oily residue. The oily residue is taken up in methylene chloride, filtered, concentrated and dried in a high vacuum to yield the heading compound as a yellow oil.

(d) L-Phenylalanyl-L-proline tert.-butyl ester [compound of formula VI]

223 g of N-carbobenzoxy-L-phenylalanyl-L-proline tert.-butyl ester is hydrogenated in analogous manner to step (b), using 2100 ml absolute tetrahydrofuran as solvent instead of ethanol, to give the heading compound as a colourless oil.

(e) N-(N-carbobenzoxy-D and L-α-methylseryl)-L-phenylalanyl-L-proline tert.-butyl esters [Tripeptide esters I and II] [compounds of formula V]

7.2 g of N-carbobenzoxy-DL-α-methylserine is reacted with 9.5 g of L-phenylalanyl-L-proline tert.-butyl ester in the presence of 6.8 g N,N-dicyclohexylcarbodiimide and worked up as described in step (c). The resultant oil is chromatographed on silica gel, using methylene chloride containing 1% methanol as eluant. One of the heading compounds (tripeptide ester I) is first eluted. This compound is obtained in amorphous form having $[\alpha]_{20}^D = -28.2°$ (c = 2 In $CH_2Cl_2$). Further elution using methylene chloride with increasing amounts (1–4% v/v) of methanol yields the second of the heading compounds (tripeptide ester II) which is crystallized from ethyl acetate/hexane (1:3 v/v); M.Pt. 120°–121° $[\alpha]_D^{20} = -48.4°$ (c = 2 in $CH_2Cl_2$).

(f) N-(N-carbobenzoxy-D and L-α-methylseryl)-L-phenylalanyl-L-proline diasteroisomers [Tripeptides I and II] [compounds of formula IV]

(fi) Tripeptide I 2.2 g of the amorphous tripeptide ester I obtained in step (e) is dissolved in 3 ml trifluoroacetic acid and maintained at room temperature for ¾ hour. The mixture is concentrated under a high vacuum at room temperature. The resulting residue is taken up in methylene chloride. The mixture is made alkaline by the addition of potassium bicarbonate solution, and the resultant mixture is extracted three times with a mixture of methylene chloride containing a little ethanol. The organic phases are washed twice with a dilute potassium bicarbonate solution. The aqueous washings are made alkaline with 16% (w/v) hydrochloric acid and then extracted three times with methylene chloride. The organic phases are washed once with water, dried with sodium sulphate and concentrated. Crystallization of the resultant foam from a mixture of methylene chloride, some methanol, and ethyl acetate gives the pure tripeptide I as white crystals; M.Pt. 134°–136° $[\alpha]_D^{20} = -30.0°$ (c = 2 in $C_2H_5OH$).

(fii) Tripeptide II

This is obtained analogous to (fi) as white crystals from ethyl acetate/diisopropyl ether (1:1); M.Pt. 115°–118° $[\alpha]_D^{20} = -38°$ (c = 1.5 in $C_2H_5OH$).

(g) N-(N-carbobenzoxy-D and L-α-methylseryl)-L-phenylalanyl-L-proline p-nitrophenyl esters [Tripeptide nitrophenyl esters I and II] [compounds of formula III]

(gi) Tripeptide nitrophenyl ester I 24.7 g of dicyclohexylcarbodiimide in 200 ml of absolute methylene chloride and 50 ml of absolute diethyl ether is added to a solution of 49.7 g of the tripeptide I obtained in step (fi) and 34.8 g of nitrophenol in 200 ml of methylene chloride. The resultant yellow suspension is stirred at 20° for 2 hours. Ten minutes after the addition of 5 ml 40% (w/v) acetic acid, the mixture is filtered, the solid residue being washed with methylene chloride. The yellow filtrate is washed three times with a 20% (w/v) potassium bicarbonate solution, the aqueous phase being extracted twice with methylene chloride. The combined aqueous phases are dried over sodium sulphate and concentrated to a solid yellow residue. The residue is dissolved in methylene chloride/diethyl ether (1:1 v/v) and chromatographed on silicagel.
After elution with diethyl ether containing 2% acetonitrile, the tripeptide nitrophenyl ester I is obtained by eluting with diethyl ether containing 6-10% acetonitrile.

(gii) Tripeptide nitrophenyl ester II

This is obtained analogous to step (gi) and is crystallized from acetone/hexane to give colourless needles; M.Pt. 100°-101.5°; $[\alpha]_D^{20} = -70.5°$ (c = 1, $CH_2Cl_2$).

(h)
N-(N-carbobenzoxy-DL-α-hydroxyalanyl)-L-phenylalanyl-L-proline p-nitrophenyl ester [compound of formula II]

(hi) from Tripeptide nitrophenyl ester I 75 ml of absolute benzene and 7.5 g Linde molecular sieve 4A are placed in a pre-dried vessel. After 1 hour 5.32 g lead acetate which has been dried under a high vacuum is added and the mixture is stirred for 30 minutes. 6.18 g of tripeptide nitrophenyl ester I obtained in step (gi) in 50 ml absolute benzene is added. The mixture is immediately heated to the boiling temperature and maintained for 10 minutes under reflux. The mixture is cooled to 15° with an ice bath, and filtered. The filtrate is washed with benzene and partitioned between methylene chloride and ice water. The methylene chloride phase is filtered through active charcoal, and concentrated at 35° to yield the heading compound as a colourless foam.

(hii) from Tripeptide nitrophenyl ester II

In analogous manner the heading compound is obtained from tripeptide nitrophenyl ester II obtained in step (gii).

(hiii) from Tripeptide nitrophenyl ester I and II mixture

If desired, steps (e), (f) and (g) may be effected without separating the tripeptide esters I and II in step (e), the tripeptides I and II in step (f) and tripeptide nitrophenyl esters I and II in step (g), to produce the heading compound in step (h).

The N-carbobenzoxy-DL-α-methylserine (compound of formula VII), used as starting material in step (e) may be obtained as follows:

23.9 g of DL-α-methylserine is treated with 160 ml absolute pyridine. 68 g of carbobenzoxy chloride is added dropwise over 20 minutes to the mixture at 20° to 25°. The mixture is maintained for 6 hours at room temperature and then a further 34 g of carbobenzoxy chloride is added. The mixture is stirred overnight, and then 400 ml of 2N sodium carbonate solution is carefully added. The mixture is washed twice with diethyl ether and the organic phases are washed once with sodium carbonate solution. The combined sodium carbonate phases are adjusted to pH 1 by the addition of concentrated hydrochloric acid/ice (1:1 v/v). The mixture is extracted three times with ethyl acetate. The ethyl acetate phases are washed with saturated sodium chloride solution, dried and concentrated to give the heading compound; M.Pt. 115°-116° (from ethyl acetate/diisopropyl ether, 1:4).

In analogous manner to that described in Example 1, and using the appropriate reagents in steps (g) and (h), the title compound may be obtained from the corresponding compounds of formulae IIa and IIb, wherein $R_6$ is:
(a) phenylthio
(b) pentafluorophenoxy
(c) pentachlorophenoxy
(d) p-chlorophenylthio
(e) o-nitrophenoxy
(f) o,p-dinitrophenoxy
(g) o-methyl-o',p'-dinitrophenoxy.

EXAMPLE 2

Natural (2R,5S,10aS,10bS) form of
2-carbobenzoxyamino-2-methyl-5-benzyl-10b-hydroxy-3,6-dioxo-octahydro-8H-oxazolo[3,2-a]pyrrolo[2,1-c]pyrazine from the corresponding aci form 2.2 g of aci-2-carbobenzoxyamino-2-methyl-5-benzyl-10b-hydroxy-3,6-dioxo-8H-oxazolo[3,2-a]pyrrolo[2,1-c]pyrazine (see Example 1) is suspended in 13 ml acetic acid, 90 ml of dioxane and 100 ml water. The mixture is boiled until a clear colourless solution results, and then boiled for a further 5 hours. The mixture is cooled, diluted with water, and extracted with methylene chloride. The organic extracts are concentrated, unreacted starting material crystallizing out. The mother liquors are chromatographed on aluminium oxide, eluting with methylene chloride containing 0.4% methanol the title compound; M.P. 171°-172.5°.

EXAMPLE 3

In analogous manner to Example 1 the following natural and aci forms of N-benzoxycarbonyl aminocyclols of formula I, wherein $R_1$ is $C_6H_5CH_2OCO$ are produced showing no depression of the melting point on admixture with authentic material, and aci forms may be converted into the corresponding natural form in analogous manner to Example 2.

|    | $R_2$ | $R_3$ | $R_4$ | $R_5$ |
|----|-------|-------|-------|-------|
| a) | iso-$C_3H_7$ | H | $C_6H_5CH_2$ | H |
| b) | iso-$C_3H_7$ | H | iso-$C_3H_7$ | H |
| c) | $CH_3$ | H | iso-$C_3H_7$ | H |
| d) | $CH_3$ | $CH_3$ | $CH_3$ | H |
| e) | $CH_3$ | H | iso-$C_4H_9$ | H |
| f) | $CH_3$ | H | p-$CH_3O$-$C_6H_4CH_2$ | H |
| g) | $CH_3$ | $CH_3$ | $C_6H_5 \cdot CH_2$ | H |
| h) | $CH_3$ | H | $C_6H_5 \cdot CH_2$ | $CH_3$ |
| i) | $C_2H_5$ | H | $C_6H_5 \cdot CH_2$ | H |
| j) | $C_2H_5$ | H | iso-$C_3H_7$ | H |
| k) | $C_2H_5$ | H | iso-$C_4H_9$ | H |
| l) | iso-$C_3H_7$ | $CH_3$ | $C_6H_5 \cdot CH_2$ | H |
| m) | iso-$C_3H_7$ | H | n-$C_3H_7$ | H |
| n) | iso-$C_3H_7$ | H | sec-$C_4H_9$ | H |
| o) | iso-$C_3H_7$ | H | iso-$C_4H_9$ | H |
| p) | n-$C_3H_7$ | $CH_3$ | $CH_3$ | H |
| q) | $C_2H_5$ | $CH_3$ | $CH_3$ | H |
| r) | $CH_3$ | H | sec-$C_4H_9$ | H |

The DL-α-isopropylserine used as starting material for Example 1( e) may be obtained as follows:
96 g L-valine and 96 g sodium carbonate in 3 liters of water is treated with 22.5 g of $CuSO_4 \cdot 5H_2O$ and 500 ml of 35% (w/v) formaldehyde solution. The resultant mixture is boiled under nitrogen for 1½ hours to give a colourless solution (pH 9). 11.5 g CuSO₄.5H₂O is then added and the mixture is boiled for a further hour to give a solution having pH 7.3. After cooling the solution is filtered, adjusted to pH 4 with acetic acid and applied to a column of H⁺ ion exchange resin, e.g. Amber-lite IR 120 (H⁺ form). The column is washed neutral with water and then eluted with 10% (w/v) ammonia. The ninhydrin - positive fractions were combined, concentrated to 50 ml, and diluted with absolute ethanol to give the heading compound; M.Pt. 302°–303° (decomp.) (from water/ethanol and after drying in a high vacuum).

I claim:

1. A process for the production of an aminocyclol of formula I

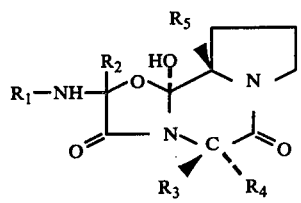

where
  R₁ is an amino protecting group of lysergic acid residue,
  R₂ is alkyl of 1 to 4 carbon atoms,
  R₃ and R₅ are each independently hydrogen or alkyl of 1 to 5 carbon atoms,
  R₄ is hydrogen, alkyl of 1 to 6 carbon atoms, phenyl, benzyl or benzyl monosubstituted by alkoxy of 1 to 4 carbon atoms,
which comprises the steps of intramolecularly cyclizing a compound of formula II

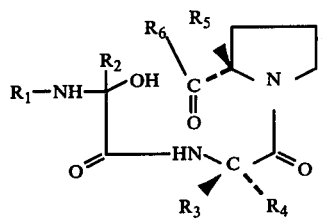

wherein
  R₁ to R₅ are as defined above and
  R₆ is N-succinimidoxy, phenoxy, phenythio, phenoxy or phenylthio independently substituted with 1 to 3 substituents selected from methyl, halogen and nitro or phenoxy or phenythio substituted with 1 to 5 fluoro or chloro substituents,
by splitting off R₆H under mild solvolytic conditions.

2. A process according to claim 1, wherein the compound of formula II is prepared by oxidizing or hydrolyzing under mild conditions a compound of formula III

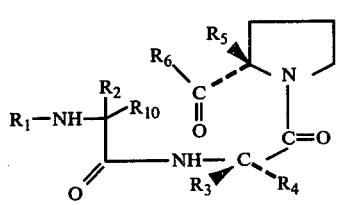

wherein
  R₁ to R₄ are as defined in claim 1 and R₁₀ is halo, isocyanate, -CH(CH₃)-OH an -CH₂OH.

3. A process according to claim 1, wherein the aminocyclol in the natural form, having the formula

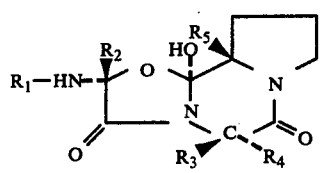

is prepared by intramolecularly cyclizing a compound of formula IIa

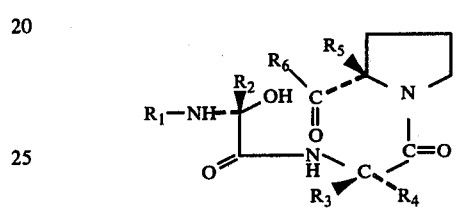

where R₁ to R₆ are as defined in claim 1.

4. A process according to claim 1, wherein the aminocyclol in the aci form, having the formula

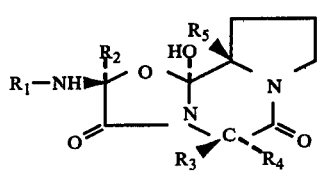

is prepared by intramolecularly cyclizing a compound of formula II b

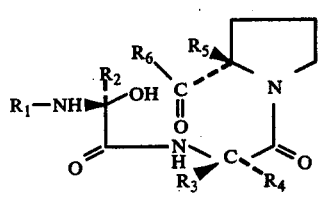

wherein R₁ to R₆ are as defined in claim 1.

5. A process according to claim 1, wherein the aminocyclol is a mixture of the natural form, having the formula

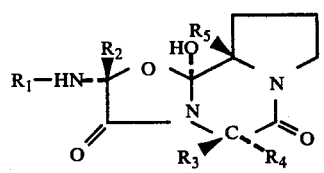

and the aci form, having the formula

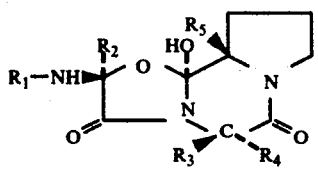 Ib and is prepared by intramolecularly cyclizing a mixture of a compound of formula II a

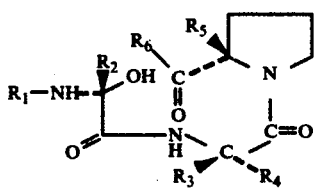 IIa and II b,

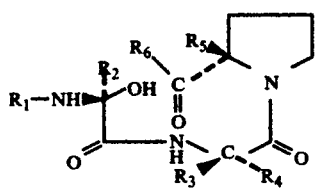 IIb wherein $R_1$ to $R_6$ are as defined in claim 1.

6. A process according to claim 5, in which the natural form is separated from the aci form.

7. A process according to claim 6, wherein the aci form is converted into the natural form by rearrangement under mild acidic conditions.

8. A process for preparing a compound of the formula

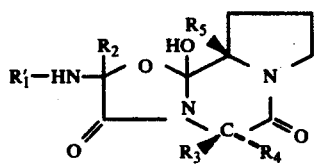

where $R_1'$ is a lysergic acid residue which comprises removing the amino protecting group, $R_1$, from a compound of the formula

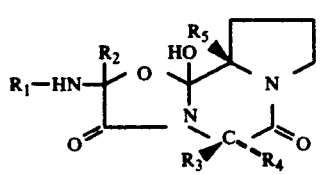

to obtain an aminocyclol of the formula

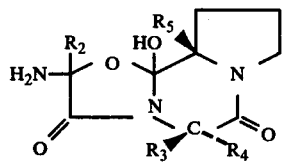

where $R_1$ to $R_5$ are as defined in claim 1, and thereafter reacting the aminocyclol with lysergic acid or a reactive functional derivative of lysergic acid.

9. A compound of formula II

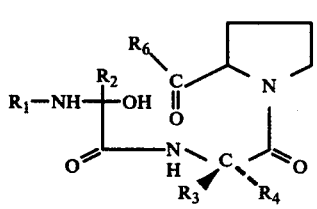 II where $R_1$ to $R_6$ are as defined in claim 1.

10. A process according to claim 2, wherein $R_{10}$ is halogen.

11. A process according to claim 2, wherein $R_{10}$ is isocyanate.

12. A process according to claim 2, wherein $R_{10}$ is $CH_2OH$.

13. A process according to claim 2, wherein $R_{10}$ is $CH(CH_3)$—OH.

14. A process according to claim 1, wherein $R_6$ is N-succinimidoxy, pentafluorophenoxy, pentachlorophenoxy, a radical A,

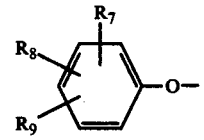 A wherein
$R_7$ is nitro,
$R_8$ is hydrogen, chlorine, or methyl, and
$R_9$ is hydrogen or nitro,
or p-chlorophenylthio.

15. A process according to claim 1, wherein $R_6$ is o,p-dinitrophenoxy, o-methyl-o'-p'-dinitrophenoxy or pentachlorophenoxy.

16. A process according to claim 1, wherein $R_6$ is p-nitrophenoxy.

17. A process according to claim 4, wherein the aci form of the aminocyclol is converted into the natural form by rearrangement under mild acidic conditions.

18. A process according to claim 39, wherein $R_1$ is an amino protecting group which is removable under hydrogenolytic conditions.

19. A process according to claim 1, wherein $R_1$ is a lysergic acid residue.

20. A process according to claim 1, wherein $R_1$ is a lysergic acid residue in which the 2-nitrogen is protected by an amine protecting group.

21. A process according to claim 1, wherein $R_1$ is a 2,3-dihydrolysergic acid residue.

22. A process according to claim 1, wherein $R_1$ is a 1-acetyl-2,3-dihydrolysergic acid residue.

* * * * *

UNITED STATES PATENT AND TRADEMARK OFFICE
CERTIFICATE OF CORRECTION

PATENT NO. : 4,145,549
DATED : March 20, 1979
INVENTOR(S) : Paul Stadler

It is certified that error appears in the above-identified patent and that said Letters Patent are hereby corrected as shown below:

Col. 4, please delete the formula between lines 3-13, and insert in its place the correct formula:

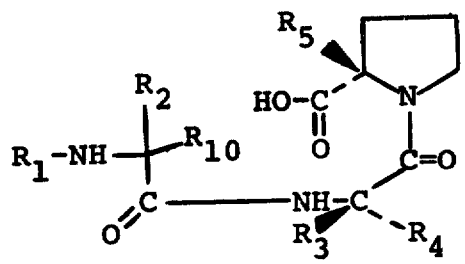

Col. 11, claim 1, line 26, delete the word "of" and insert in its place the correct word -- or --.

Col. 12, line 2, delete "$R_4$" and insert in its place the correct designation -- $R_6$ --.

Col. 12, line 3, delete the word "an" and insert in its place the correct word -- or --.

Col. 14, line 56, claim 18, delete the number "39" and insert in its place the correct number -- 1 --.

Signed and Sealed this

Eighth Day of January 1980

[SEAL]

Attest:

SIDNEY A. DIAMOND

Attesting Officer

Commissioner of Patents and Trademarks